United States Patent
Schwarzentruber et al.

(10) Patent No.: US 8,187,589 B2
(45) Date of Patent: May 29, 2012

(54) STABILISATION OF AQUEOUS MINERAL PREPARATIONS BY REUTERIN

(75) Inventors: Patrick Schwarzentruber, Habsburg (CH); Nicola Di Maiuta, Zuchwil (CH)

(73) Assignee: Omya Development AG, Oftringen (CH)

( * ) Notice: Subject to any disclaimer, the term of this patent is extended or adjusted under 35 U.S.C. 154(b) by 0 days.

(21) Appl. No.: 12/737,741

(22) PCT Filed: Aug. 19, 2009

(86) PCT No.: PCT/EP2009/060737
§ 371 (c)(1),
(2), (4) Date: Apr. 21, 2011

(87) PCT Pub. No.: WO2010/023143
PCT Pub. Date: Mar. 4, 2010

(65) Prior Publication Data
US 2011/0197781 A1    Aug. 18, 2011

Related U.S. Application Data

(60) Provisional application No. 61/190,951, filed on Sep. 4, 2008.

(30) Foreign Application Priority Data

Aug. 28, 2008    (EP) ..................................... 08163214

(51) Int. Cl.
*A01N 63/02* (2006.01)
*D21H 21/36* (2006.01)
*C09C 1/00* (2006.01)
*C09C 1/02* (2006.01)

(52) U.S. Cl. .................. 424/93.45; 106/15.05; 106/417; 106/447; 106/461; 106/465; 106/491; 106/795; 106/801; 106/802; 106/811; 106/814; 106/817

(58) Field of Classification Search ............... 106/15.05, 106/417, 447, 461, 465, 491, 795, 801, 802, 106/811, 814, 817; 424/93.45
See application file for complete search history.

(56) References Cited

U.S. PATENT DOCUMENTS

| | | | | |
|---|---|---|---|---|
| 5,352,586 A | * | 10/1994 | Dobrogosz et al. | 435/34 |
| 5,413,960 A | * | 5/1995 | Dobrogosz et al. | 435/189 |
| 5,439,678 A | * | 8/1995 | Dobrogosz et al. | 424/93.45 |
| 5,849,289 A | * | 12/1998 | Dobrogosz et al. | 424/93.45 |
| 2005/0123583 A1 | * | 6/2005 | Sung et al. | 424/426 |
| 2007/0264401 A1 | * | 11/2007 | Taormina et al. | 426/532 |
| 2007/0275140 A1 | * | 11/2007 | Safko | 426/330.3 |

FOREIGN PATENT DOCUMENTS

| DK | 173239 B1 | 5/2002 |
|---|---|---|
| EP | 0 698 347 A2 | 2/1996 |
| WO | WO88/08452 A1 * | 11/1988 |

OTHER PUBLICATIONS

European Search Report dated Mar. 16, 2009 in connection with European Patent Application No. 08163214.3, 4 pages.
International Search Report dated Sep. 23, 2009 for PCT Application No. PCT/EP2009/060737.
Written Opinion of the International Searching Authority for PCT Application No. PCT/EP2009/060737, Sep. 23, 2009.
Rasch "The influence of temperature, salt and pH on the inhibitory effect of reuterin on *Escherichia coli*." Intl. J. of Food Micro. 72 (2002) pp. 225-231.

* cited by examiner

*Primary Examiner* — Anthony J Green
(74) *Attorney, Agent, or Firm* — Amster, Rothstein & Ebenstein LLP

(57) ABSTRACT

The present invention relates to a process for stabilizing aqueous preparations of minerals by adding reuterin to the aqueous preparations, to the use of reuterin for the stabilization of such aqueous mineral preparations, and the aqueous mineral preparations containing reuterin.

22 Claims, No Drawings

STABILISATION OF AQUEOUS MINERAL PREPARATIONS BY REUTERIN

This is a U.S. national phase of PCT Application No. PCT/EP2009/060737, filed Aug. 19, 2009, which claims priority to European Application No. 08163214.3, filed Aug. 28, 2008, and U.S. Application No. 61/190,951, filed Sep. 4, 2008.

The present invention relates to a process for stabilizing an aqueous preparation of minerals with respect to microbicides, to the use of reuterin for the microbial stabilization of such aqueous mineral preparations, and the aqueous mineral preparations containing reuterin.

In practice, aqueous preparations and especially suspensions, dispersions or slurries of water-insoluble solids such as minerals, fillers or pigments are used extensively in the paper, paint, rubber and plastics industries as coatings, fillers, extenders and pigments for papermaking as well as aqueous lacquers and paints. For example, suspensions or slurries of calcium carbonate, talc or kaolin are used in the paper industry in large amounts as filler and/or as a component in the preparation of coated paper.

Typical aqueous preparations of water-insoluble solids are characterized in that they comprise water, a water-insoluble solid compound and optionally further additives in the form of a suspension, a slurry or dispersion with a water-insoluble solid content of 1 to 80 wt.-% based on the total weight of the preparation.

A typical aqueous preparation is a White Mineral Dispersion (WMD) having a solids content of 45-78 wt.-%. It is also well known that such high solids WMD are stabilized with dispersants like sodium polyacrylates as, for example, described in U.S. Pat. No. 5,432,239.

The aforementioned aqueous preparations are often subject to contamination by microorganisms such as aerobic and anaerobic bacteria, fungi, algae and the like resulting in changes in the preparation properties such as changes in viscosity and/or pH, discolorations or reductions in other quality parameters, which negatively affect their commercial value. Therefore, the manufacturers of such aqueous preparations usually take measures for stabilizing the suspensions, dispersions or slurries. For example, it is known that aldehyde-releasing biocides reduce the growth and accumulation of such microorganisms in aqueous preparations and, thus, reduce the tendency of undesired alterations of these preparations, like viscosity changes or unpleasant odours.

For ensuring an acceptable microbiological quality of aqueous preparations, preservatives or biocides are used over the entire life cycle of the preparation (production, storage, transport, use). In the art, several approaches for improving the microbiological quality of aqueous preparations have been proposed.

For example, EP 1 139 741 and EP 1 283 822 describe aqueous suspensions or dispersions of minerals, fillers and/or pigments, containing a microbicidal agent in the form of a solution and derivatives of phenol in partially neutralized form.

U.S. Pat. No. 5,496,398 relates to a process for the reduction of microorganisms in kaolin clay slurries by a combination of low temperature heat and reduced levels of a microbicidal agent.

WO 02/052941 describes biocide compositions for incorporation into paints, coating, plasters and plastics comprising at least one metal oxide and at least one metal salt.

US 2006/0111410 mentions a mixture comprising 1,2-benzisothiazolinone (BIT) and tetramethylolacetylenediurea (TMAD) for protecting industrial materials and products against attack and destruction by microorganisms.

Furthermore, it is suggested in the art to add formaldehyde-releasing substances to such aqueous preparations for improving the microbiological quality. For example, U.S. Pat. No. 4,655,815 mentions an antimicrobial composition comprising a formaldehyde donor.

Furthermore, WO 2006/079911 describes a method of protection against microorganisms by increasing the $OH^-$ ion concentration of the suspension.

However, because of the limited activity spectrum of several biocides, the efficacy of such biocides against microorganisms (mainly certain species of bacteria) is not always satisfactory, and, thus, the obtained action is in some cases insufficient to avoid microbially induced alteration of aqueous mineral preparations.

Generally, the use of "natural" microbicides such as reuterin is advantageous due to their easy and environmentally friendly accessibility.

However, many of the commonly used natural microbicides are not suitable to be used in aqueous mineral preparations due to the usually high pH values of such preparations and their complex chemistry.

The pH is not only important with respect to the stability of the biocidal formulation, but also with respect to the medium in which it is used. Because of the instability of many microbicides at a high pH, they are often formulated in a slightly acidic medium. This, however, causes an undesired change of the pH of the preparation to be stabilized.

Furthermore, many microbicides suffer from multiple resistances of the microbes to be treated, such that there is a continuous need for new and effective microbicides for the use in different media.

Reuterin is known for its antimicrobial properties in other technical fields such as the food industries and has a broad spectrum of microbial activity. It comprises a mixture of substances produced by Lactobacillus reuteri, a naturally occurring substance residing in the gastrointestinal tract of humans and animals, from glycerol.

Reuterin is known to inhibit the growth of some harmful gram-negative and gram-positive bacteria, along with yeast, fungi and protozoa.

Reuterin, however, is rather sensitive with respect to high pH values as well, and up to now is only known as a preservative in the food industry, drug delivery, biomedical materials, and as a dietary supplement, being a low cytotoxic substance (e.g. it is less cytotoxic than high molecular weight aldehydes).

For example, U.S. Pat. No. 5,849,289 and JP 8289769 describe preservatives for foods having a wide antimicrobial activity without affecting the quality of food by blending reuterin obtained from Lactobacillus reuteri with an emulsifier for food such as monoglycerides of fatty acids, glycerine fatty acid esters or saccharide fatty acid esters.

In EP 0 698 347 a food composition comprising Lactobacillus reuteri is described producing reuterin in the presence of glycerol or glyceraldehyde for the alleviation of gastrointestinal disorders.

However, no description could be found that reuterin could also be used advantageously in aqueous mineral preparations.

To the contrary, e.g. in "Production and Isolation of Reuterin, a Growth Inhibitor Produced by *Lactobacillus reuteri*" (Talarico T. et al., Antimicrobial Agents and Chemotherapy, Dec. 1988, Vol 32, No. 12, p. 1854-1858) it is even shown that reuterin degrades upon exposure to an alkaline environment at 37° C.

Moreover, strains of microbes existing in aqueous mineral preparations generally differ from those found in a food environment, namely because of the higher pH, lower water content and poor nutrient content of the aqueous mineral preparations.

Thus, there is a continuous need for a method to reduce the growth and accumulation of microorganisms in aqueous preparations containing minerals, reducing the tendency of alterations of these preparations, and maintaining the desired viscosity and pH, the brilliance and colour and preventing bad odour, by microbicides which are suitable for the use in aqueous mineral preparations.

Accordingly, it is an object of the present invention to provide a process for effectively stabilizing aqueous preparations containing minerals with respect to microbes by an easily accessibly microbicide, also at high pH values, as well as to provide the resulting aqueous preparations.

Furthermore, another object of the present invention is the use of alternative microbicides for stabilizing aqueous preparations containing minerals, being easily accessible and applicable and having good application characteristics.

It was surprisingly found that reuterin can be advantageously used for the microbial stabilisation in the complex environment of aqueous mineral preparations.

Thus, the above and other objects have been solved by a process for stabilizing aqueous preparations of minerals with respect to microbes contained therein by the addition of reuterin to the aqueous preparations.

In the context of the present invention "stabilisation" comprises disinfection and preservation against and any kind of control of the microbial contamination of aqueous mineral preparations.

Aqueous mineral preparations according to the present invention are any kind of aqueous dispersions, suspensions or slurries of minerals, in an aqueous medium.

It is preferred that the minerals contained in the aqueous preparation are selected from the group comprising natural minerals, synthetic minerals, fillers or pigments such as dry and wet ground natural calcium carbonate such as chalk, limestone, calcite, marble and dolomite; precipitated calcium carbonate in its aragonitic, calcitic and vateritic form; calcium sulfate; quartz; attapulgite; clays such as kaolin, kaolinitic clay, calcined kaolinitic clay and montmorillonite; mica; talc; diatomaceous earth; finely divided silica; aluminium oxide; aluminium hydroxide; silicates such as aluminium silicate; iron oxide; titanium dioxide; pumice; sepiolite, and mixtures thereof as well as composite materials comprising one or more of the afore-mentioned substances, e.g. pigment composites including precipitated calcium carbonate, mica, titanium dioxide, and mixtures thereof.

Preferably, the aqueous preparation is a "white mineral dispersion" (WMD), comprising dispersions of calcium carbonate such as natural calcium carbonate, ground calcium carbonate, precipitated calcium carbonate, kaolin, dolomite, kaolinitic clay, calcined kaolinitic clay or mixtures thereof.

Calcium carbonate, is used e.g. as a coating and filling pigment, and is notably known to improve the optical properties of the final product, such as gloss, opacity or brightness.

Calcium carbonate can be of two types: ground or natural calcium carbonate referred to as GCC and NCC, respectively, and synthetic or precipitated calcium carbonate referred to as PCC.

PCC in the meaning of the present invention is a synthetic material, generally obtained by precipitation due to the reaction of carbon dioxide and lime in an aqueous environment or by precipitation of a calcium and carbonate ion source in water. It may have rhombohedral, scalenohedral, aragonitic, calcitic and/or vateritic structure.

NCC in the meaning of the present invention is a calcium carbonate obtained from natural sources such as limestone, marble, chalk or dolomite, and can be processed by a treatment such as grinding, screening and/or fractionizing by wet and/or dry methods, for example by a cyclone or classifier.

Ground natural calcium carbonate generally is referred to as GCC.

Any of the above mentioned materials useful in the present invention may additionally be surface treated, for example with fatty acids, such as stearic acid, and their salts. Calcium carbonates furthermore can be surface-reacted, e.g. with medium to strong acids such as phosphoric acid. Also, composites comprising calcium carbonate may be used.

Clay generally refers to crystalline small particles of mainly hydrous silicates of aluminium, sometimes with magnesium and/or iron substitution for all or a part of the aluminium. The main groups of clay minerals are: kaolinite, the main constituent of kaolin; halloysite; illite; montmorillonite and vermiculite. The term "kaolinitic clay" used herein refers to a soft white clay that is composed mainly of the mineral kaolinite.

Kaolin is especially used in the paper industry for coating and filling papers and boards and improving the optical properties of the final product such as gloss, opacity or brightness. However, kaolin based products also include paints, agricultural compositions, fibre glass products, polymer and rubber compositions, ceramic applications, catalyst supports, pharmaceuticals, cosmetics, adhesives, filter aids, and many more.

In a specific embodiment the aqueous mineral preparation is a calcium carbonate dispersion comprising precipitated calcium carbonate. In this case, reuterin can be added before, during and/or after the precipitation of the calcium carbonate, or any other mineral obtained by precipitation.

Also, naturally occurring ground calcium carbonate might be comprised in the aqueous preparation, in which case the reuterin can be added before, during and/or after grinding of the calcium carbonate or any other mineral subjected to comminution steps such as grinding.

The addition of reuterin to the aqueous mineral preparation according to the invention can be carried out by methods known in the art, for example by dispersing, suspending or slurrying water-insoluble solids, preferably minerals, pigments or fillers, with, if appropriate, addition of a dispersing agent and, if appropriate, further additives in water. Insoluble in the meaning of the present invention means that not more than 1 wt.-%, preferably 0.1 wt.-%, more preferably 0.01 wt.-% of the solids, preferably minerals, pigments or fillers, is dissolved.

An aqueous preparation according to the present invention comprises insoluble mineral solids, water and optionally further additives.

Preferably, the aqueous mineral preparation has a solids content from 40 to 85 wt.-%, more preferably from 45 to 82 wt.-%, especially from 70 to 80 wt.-%, particularly from 72 to 78 wt.-%, e.g. 75 wt.-% of the total weight of the preparation.

The water content of the aqueous mineral preparation preferably is from 15 to 60 wt.-%, more preferably from 18 to 55 wt.-%, especially from 20 to 30 wt.-%, particularly from 22 to 28 wt.-%, e.g. 25 wt.-% of the total weight of the preparation.

The total solids content in the meaning of the present application corresponds to the residual weight of the preparation after drying for 3 hours at 105° C.

The water-insoluble solids in the preparation may have a particle size distribution as conventionally employed for the material(s) involved in this type of product. In general, 90 wt.-% of the particles will have an "esd" (equivalent spherical diameter as measured by the well known technique of sedimentation using Sedigraph 5100 series, Micromeritics) of less than 5 μm. Coarse minerals, filler or pigment materials may have a particle esd of generally (i.e. at least 90 wt.-%) in the range of 2 to 5 μm. Fine minerals, filler or pigment materials may have a particle esd generally less than 2 μm, e.g. 90 wt.-% less than 2 μm.

It is preferred that the solid particles in the preparation have a $d_{50}$ value of from 0.1 to 50 μm, preferably from 0.2 to 6 μm and most preferably from 0.4 to 2 μm, for example 0.7 μm as measured using a Sedigraph™ 5100 of Micromeritics Instrument Corporation. The method and the instrument are known to the skilled person and are commonly used to determine grain sizes of fillers and pigments. The measurement is carried out in an aqueous solution of 0.1 wt.-% $Na_4P_2O_7$. The samples are dispersed using a high speed stirrer and supersonics.

The microbial stabilization of the above mentioned mineral preparations, especially carbonate dispersions, by reuterin is especially surprising in view of the fact that the pH in these suspensions is usually high.

The pH value of the mineral preparations according to the invention may be in the range of from above 7 to 10.5, preferably from 8.5 to 10, e.g. 9 to 9.5 as measured at 25° C.

Typically, the aqueous preparations according to the present invention have a viscosity in the range of from 50 to 800 mPa·s and preferably 150 to 600 mPa·s, as measured with a Brookfield DV-II Viscometer at a speed of 100 rpm and equipped with a LV-3 spindle.

Reuterin useful in the present invention comprises 3-hydroxypropionaldehyde, such as monomeric 3-hydroxypropionaldehyde ("monomer"), hydrated monomeric 3-hydroxypropionaldehyde ("hydrate"), dimeric 3-hydroxypropionaldehyde ("dimer"), or cyclic forms thereof or mixtures thereof Usually, 3-hydroxypropionaldehyde forms a dynamic multi-component equilibrium together with the hydrate and the dimmer, the ratios of which can vary over a wide range.

Reuterin, which is especially suitable for the stabilization of the aqueous mineral preparations according to the invention can generally be obtained by several pathways, preferably involving glycerol dehydratase (EC 4.2.1.30) transforming glycerol into reuterin. It may be produced naturally by fermentation and/or synthetically, e.g. passing from glycerol via acrolein (of a petrochemical or non-petrochemical source) and by hydrolysis, to reuterin.

For the present invention, Reuterin coming from any source is generally suitable. However, from an economical and environmental point of view, it is especially preferred to use reuterin coming from the microbial transformation of glycerol.

In vivo, active reuterin synthesis occurs in the gastrointestinal tract, e.g. in the colon via *Lactobacillus reuteri* metabolism, if sufficient amounts of glycerol become available as a product of luminal microbial fermentations, digestion of luminal fats, sloughed mucus and desquamated epithelial cells, and intestinal clearing of endogenous plasma glycerol.

In vitro, reuterin can be synthesized from glycerol and, preferably, *Lactobacillus reuteri* under pH, temperature and anaerobic conditions similar to those of the gastrointestinal tract.

Reuterin useful in the present invention can be naturally obtained or synthesized reuterin, wherein, for practical reasons, synthetic reuterin is preferred.

There are several *Lactobacillus reuteri* strains, which are useful in the production of reuterin, e.g. DSM 8533, DSM 8534, DSM 8535, DSM 17509, DSM 20016, DSM 20053, DSM 20056, and/or ATCC 23272, ATCC 53608, ATCC 53609, ATCC 55148, ATCC 55739, wherein the strains DSM 20016, and ATCC 23272, ATCC 53608, ATCC 53609, respectively, are especially suitable.

There is a number of publications describing the production of reuterin by Lactobacillus reuteri from glycerol. Methods suitable for the use in the present invention are described for example, but not exclusively, in: Y. Doleyres et al., Appl Microbiol Biotechnol (2005) 68; p. 467-474; T. L. Talarico et al., Antimicrobial Agents and Chemotherapy, Dec. 1998, p. 1854-1858; A. S. Sani et al., paper, $9^{th}$ International Conference on Agricultural Biotechnology: Ten Years After (ICABR), Ravello (Italy), 6-10 Jul. 2005; Q. Lüthi-Peng; Appl Microbiol Biotechnol (2002) 60; p. 73-80.

Reuterin is added to the aqueous preparation in an effective amount. In the meaning of the present invention, an "effective amount" of reuterin corresponds to an amount which at the time of addition leads to a measurable biocidal activity (e.g. reduction or prevention of the growth and/or accumulation of microorganisms) in an aqueous preparation in comparison to a corresponding preparation containing no reuterin or any other biocidal compounds.

Reuterin to be mixed with the aqueous mineral preparation to be stabilized, preserved or controlled with respect to its microbial contamination can be added in any desired ratio to achieve the desired biocidal activity.

It can be added once, e.g. before, during or after the manufacture of the aqueous mineral preparation, or several times, e.g. in specific time intervals, during storage or before and/or during transport of the preparations, in a manner known by the skilled person.

The reuterin concentrations to be used depend on the nature and the occurrence of the microorganisms to be controlled, the initial microbial load, and on the expected storage time of the aqueous preparations of minerals, fillers or pigments to be protected. The optimum amount to be employed can be determined by preliminary tests and test series on a laboratory scale and by supplementary operational tests.

In a preferred embodiment, a suitable amount of reuterin added to the aqueous mineral preparation is in an amount based on the eight of water of from about 100 to 5000 ppm, preferably from about 200 to 2000 ppm, more preferably from about 450 to 1000 ppm, e.g. 495 or 990 ppm.

The addition of the reuterin to the aqueous mineral preparation preferably is carried out at temperatures of from 10 to 90° C., more preferably 20 to 60° C., e.g. 30° C.

By the addition of reuterin, stabilization, preservation and/or control of the microbial contamination of aqueous mineral preparations can be provided over a long period of time.

The biocidal activity (stabilization, preservation and/or control of the microbial contamination) of aqueous mineral preparations can be provided for a time period of at least 2 days, more preferably for at least 4 days, still more preferably for at least 6 days and most preferably for a minimum of 8 days.

The addition or the use of reuterin in aqueous mineral preparations results in a reduced growth and accumulation of microorganisms and the tendency of alterations of these preparations is reduced, while low viscosity, the brilliance of the colour and the odour quality of the preparations can be maintained. Furthermore, the stabilization of such preparations against attack and destruction by microorganisms results in an enhanced microbiological quality of the preparations.

Examples of microorganisms which are able to grow and accumulate in the aqueous preparations, dispersions or slurries of minerals, fillers or pigments, and which can be controlled by the use of reuterin are in particular aerobic and anaerobic bacteria species.

The following species are known to be present in aqueous preparations of minerals, fillers or pigments: *Alcaligenes*, such as *Alcaligenes faecalis*, *Alternaria*, such as *Alternaria tenius*, *Bacteroides* such as *Bacteroides vulgatus*, *Eubacteria* such as *Eubacterium eligens*, *Pseudomonas*, such as *Pseudomonas aeruginosa*, *Pseudomonas fluorescens*, *Pseudomonas oleovorans*, *Pseudomonas mendocina*, *Pseudomonas pseudoalcaligenes*, *Pseudomonas rubescens*, *Pseudomonas stutzeri* and *Pseudomonas putida*, *Enterococci*, such as *Enterococcus faecalis*, *Enterobacter*, such as *Enterobacter aerogenes*, *Corynebacteria*, such as *Corynebacterium aquaticum*, *Citrobacter*, such as *Citrobacter freundii*, *Bacilli*, such as *Bacillus firmus* and *Bacillus subtilis*, *Desulfovibrio desulfuricans*, *Methylobacteria*, such as *Methylobacterium extorquens*. In particular, Pseudomonas aeruginosa is common in slurries, such as calcium carbonate slurries.

In view of the surprising finding that reuterin can also be effective in aqueous mineral preparations having a high pH, the use of reuterin in such aqueous mineral preparations for stabilizing same with respect to microbial growth as described in detail above is a further aspect of the present invention.

Due to the addition of reuterin, the aqueous mineral preparations according to the invention are highly resistant to attacks by microorganisms, in particular by aerobic or anaerobic bacteria species, fungi, algae and the like, thus allowing problem-free handling of the products during production, storage, transport and final use.

Thus, the aqueous preparations containing minerals and reuterin are also an aspect of the present invention.

Due to their preservation by reuterin they are especially useful in many applications, for example, in the field of paper making, paints, detergents and cosmetics, and especially in the fields requiring non-toxic microbicides, such as the food industries, house care, personal care, health care, pharmaceutical industries, medical care, etc.

The following examples and tests will additionally illustrate the invention, but are not meant to restrict the invention in any way. The examples below show the good microbiological stability of the aqueous preparations of minerals, pigments or fillers protected with the composition according to the present invention:

EXAMPLES

Example 1

1. Production of Reuterin

*Lactobacillus reuteri* (DSM 20016 strain) was grown in 2 samples of 30 ml MRS (Difco™ Lactobacilli MRS Agar (cat. No. 288130)) at 37 ° C. under aerobic conditions and with mixing at 140 rpm in 125 ml sterile media bottles.

The MRS Agar essentially had the following composition per liter:

| | |
|---|---|
| Proteose Peptone No. 3 | 10.0 g |
| Beef Extract | 10.0 g |
| Yeast Extract | 5.0 g |
| Dextrose | 20.0 g |

-continued

| | |
|---|---|
| Polysorbate 80 | 1.0 g |
| Ammonium Citrate | 2.0 g |
| Sodium Acetate | 5.0 g |
| Magnesium Sulfate | 0.1 g |
| Manganese Sulfate | 0.05 g |
| Dipotassium Phosphate | 2.0 g | pH 6.5 ± 0.2 after autoclaving at 121° C. for 15 minutes

After 24 h the cells were harvested by centrifugation at 4000 g for 10 min. at room temperature. Subsequently, each of the resulting pellets was resuspended in 5 ml of PBS (0.01 M phosphate buffered saline; available e.g. from SIGMA under product No. P3813 as powder; content of one pouch, when dissolved in one liter of distilled or deionized water, will yield 0.01 M phosphate buffered saline (NaCl 0.138 M; KCl 0.0027 M); pH 7.4, at 25 ° C.) and pooled in one tube. The pooled sample was washed twice with PBS and centrifuged at 4000g for 10 min.

The resulting pellet was then resuspended in 5 ml of 0.25 M sterile glycerol solution for its bioconversion to 3-hydroxypropionaldehyde, and the tube was incubated without cap at room temperature in an anaerobic ($N_2$) chamber for 2-3 hours at 37° C.

After the bioconversion the liquid phase is separated from the biomass by filtration using steritop™ filtration units (0.2 μm).

2. Effectivity of Reuterin in White Mineral Dispersions

Preparation of a Calcium Carbonate Slurry 10 kg of north-Norwegian marble having an esd (equivalent spherical diameter) of about 45 μm was wet ground in a recirculating, horizontal 2 liter attritor ball mill (Dynomill) using 0.6 wt.% of a radically polymerized polyacrylic acid (MW 6000 g/mol). The carboxylic acid groups of the polyacrylic acid were neutralized by 50 mole-% sodium and 50 mole-% magnesium. After grinding, the calcium carbonate slurry had the following particle size distribution:

| Diameter (μm) | wt.-% |
|---|---|
| <2 | 91.5 |
| <1 | 62.2 |
| <0.2 | 17.9 |

The particle size distribution was measured by using a Sedigraph™ 5100 of Micromeritics Instrument Corporation. The method and the instrument are known to the skilled person and are commonly used to determine grain size of fillers and pigments. The measurement is carried out in an aqueous solution of 0.1 wt.-% $Na_4P_2O_7$. The samples are dispersed using a high speed stirrer and supersonics.

The Brookfield-viscosity of the slurry was determined as 180 mPa·s, as measured with a Brookfield DV-II Viscometer equipped with a LV-3 spindle at a speed of 100 rpm and room temperature (20±3° C.).

The solids content of the slurry was determined by heating a weighed slurry sample at a temperature of 120° C. until a constant weight (within +/− 0.1%) is obtained. The percentage of remaining weight relative to the original sample weight corresponds to the solids content of the slurry. The weight lost relative during this heating process represents the water content.

Minimal Inhibition Concentration in White Mineral Dispersions 50 g of the obtained sterile slurry (solids content 75 wt-%) of ground calcium carbonate (pH 9.5) was inoculated with two different amounts, namely, based on the total weight of the slurry, 165 ppm and 330 ppm of reuterin in the form of a reuterin solution having a concentration of 110 mmol/l.

This corresponds to 495 ppm, or 990 ppm, respectively, calculated on the weight of water in the slurry.

The samples were then stored for 3 days at 30° C. under aerobic conditions. After the storage, the samples were inoculated (inoculation 1) with 1 ml of a slurry of ground calcium carbonate (60 wt-% <1 µm; 75 wt-% solids; 25 wt.-% water, pH 9.5) contaminated with a standard bacterial spectrum (>$10^5$cfu/ml ), comprising mostly *Pseudomonas* spp. (e.g. *Pseudomonas putida, Pseudomonas mendocina, Pseudomonas pseudoalcaligenes*) and incubated for 24 h at 30° C. and the total viable count was determined according to the Plate Count Method. Samples that did not show any growth (<100 cfu/ml) were further inoculated with 1 ml contaminated ground calcium carbonate slurry (60 wt-% <1 gm) (inoculations 2 and 3) and incubated for 24 h at 30° C. The total viable count was determined according to the Plate Count Method. There were no more than three inoculations performed. The results are shown in the following table.

| Reuterin batch A | Total Viable Counts [TVC · ml$^{-1}$] | | |
|---|---|---|---|
| [ppm] | 0 | 165 | 330 |
| Inoculation 1 | >>$10^4$ | <100 | <100 |
| Inoculation 2 | >>$10^4$ | <100 | <100 |
| Inoculation 3 | >>$10^4$ | <100 | <100 |

In order to confirm these results, the tests were repeated using reuterin originating from different batches B to D obtained by the above described method.

The results of these control experiments clearly proved the reproducibility of the microbicidal effectivity of reuterin in white mineral dispersions as described above and shown in the following table, which also comprises the results of a corresponding experiment of EGFH as a comparative example.

| | TVC (cfu/ml) | | | | |
|---|---|---|---|---|---|
| Reuterin batches [ppm] | 0 | B 163 ppm | C 163 ppm | D 326 ppm | control EGHF 250 ppm |
| inoculation 1 | >>$10^4$ | <100 | <100 | <100 | <100 |
| inoculation 2 | >>$10^4$ | <100 | <100 | <100 | <100 |
| inoculation 3 | >>$10^4$ | <100 | <100 | <100 | <100 |

The invention claimed is:

1. A process for treating an aqueous mineral preparation comprising contacting the preparation with a biocidal effective amount of reuterin, wherein the mineral preparation comprises a filler, a pigment, calcium carbonate, chalk, limestone, calcite, marble, dolomite, calcium sulfate, quartz, attapulgite, a clay, kaolin, kaolinitic clay, calcined kaolinitic clay, montmorillonite, mica, talc, diatomaceous earth, finely divided silica, aluminium oxide, aluminium hydroxide, a silicate, aluminium silicate, iron oxide, titanium dioxide, pumice, or sepiolite, or any mixture thereof.

2. The process according to claim 1, wherein the mineral preparation is ground natural calcium carbonate comprising chalk, limestone, calcite, marble, or dolomite or any mixture thereof.

3. The process according to claim 1, wherein the mineral preparation is precipitated calcium carbonate.

4. The process according to claim 1, wherein the mineral preparation is a calcium carbonate dispersion comprising precipitated calcium carbonate, wherein reuterin is added before, during and/or after precipitation of the calcium carbonate.

5. The process according to claim 1, wherein the mineral preparation is a calcium carbonate dispersion comprising natural calcium carbonate, wherein the reuterin is added before, during and/or after grinding of the calcium carbonate.

6. The process according to claim 1, wherein the mineral preparation comprises calcium carbonate, kaolin, dolomite, kaolinitic clay, or caolinitic clay, or any mixture thereof.

7. The process according claim 1, wherein the mineral preparation comprises a composite material comprising one or more of a filler, a pigment, calcium carbonate, chalk, limestone, calcite, marble, dolomite, calcium sulfate, quartz, attapulgite, a clay, kaolin, kaolinitic clay, calcined kaolinitic clay, montmorillonite, mica, talc, diatomaceous earth, finely divided silica, aluminium oxide, aluminium hydroxide, a silicate, aluminium silicate, iron oxide, titanium dioxide, pumice, or sepiolite.

8. The process according to claim 1, wherein the mineral preparation comprises a mineral composite comprising precipitated calcium carbonate, mica and titanium dioxide.

9. The process according to claim 1, wherein the mineral preparation comprises a mineral treated with a fatty acid.

10. The process according to claim 1, wherein the mineral preparation comprises calcium carbonate surface-reacted with a medium-strong to strong acid.

11. The process according to claim 1, wherein the mineral preparation has a solids content from 40 to 85 wt.-%, of the total weight of the preparation.

12. The preparation according to claim 1, wherein the mineral preparation has a solids content from 45 to 82 wt.-%, of the total weight of the preparation.

13. The process according to claim 1, wherein the mineral preparation has a water content of from 15 to 60 wt.-%, of the total weight of the preparation.

14. The process according to claim 1, wherein the mineral preparation has a pH in the range of from above 7 to 10.5, as measured at 25° C.

15. The process according to claim 1, wherein the reuterin is obtained from reaction of glycerol with *Lactobacillus* reuteri.

16. The process according to claim 1, wherein the reuterin comprises monomeric 3-hydroxypropionaldehyde, hydrated monomeric 3-hydroxypropionaldehyde, or dimeric 3-hydroxypropionaldehyde, or cyclic forms thereof, or any mixtures thereof.

17. The process according to claim 1, wherein the reuterin is added to the mineral preparation in an amount based on weight of water of from 100 to 5000 ppm.

18. The process according to claim 1, wherein the reuterin is added to the mineral preparation at a temperature of from 10 to 90° C.

19. An aqueous mineral preparation comprising a mineral and a biocidal effective amount of reuterin, wherein the mineral preparation comprises a filler, a pigment, calcium carbonate, chalk, limestone, calcite, marble, dolomite, calcium sulfate, quartz, attapulgite, a clay, kaolin, kaolinitic clay, calcined kaolinitic clay, montmorillonite, mica, talc, diatomaceous earth, finely divided silica, aluminium oxide, aluminium hydroxide, a silicate, aluminium silicate, iron oxide, titanium dioxide, pumice, or sepiolite, or any mixture thereof.

20. The mineral preparation according to claim 19, wherein the mineral preparation is ground natural calcium carbonate comprising chalk, limestone, calcite, marble, or dolomite or any mixture thereof.

21. The mineral preparation according to claim 19, wherein the mineral preparation is precipitated calcium carbonate.

22. The mineral preparation according to claim 19, wherein the mineral preparation comprises calcium carbonate, kaolin, dolomite, kaolinitic clay, or caolinitic clay, or any mixture thereof.

* * * * *